United States Patent [19]

Stach et al.

[11] 4,309,422
[45] Jan. 5, 1982

[54] BENZOYLHYDRAZONES OF ARYL PHOSPHATES AND PHOSPHONATES

[75] Inventors: Leonard J. Stach, Riverside; Robert N. Wilke, Oak Park, both of Ill.

[73] Assignee: Velsicol Chemical Corporation, Chicago, Ill.

[21] Appl. No.: 187,388

[22] Filed: Sep. 15, 1980

[51] Int. Cl.³ .................... C07F 9/165; A01N 57/14
[52] U.S. Cl. .................................... 424/211; 260/923
[58] Field of Search ....................... 260/923; 424/211

[56] References Cited

U.S. PATENT DOCUMENTS 3,712,914 1/1973 Tilles .................................. 260/938
4,203,932 5/1980 Brown .
4,203,979 5/1980 Brown .

FOREIGN PATENT DOCUMENTS 42-4160 2/1967 Japan .
42-6740 3/1967 Japan .

Primary Examiner—Anton H. Sutto

Attorney, Agent, or Firm—Dietmar H. Olesch; Robert J. Schwarz

[57] ABSTRACT

This invention discloses new insecticidal compounds of the formula

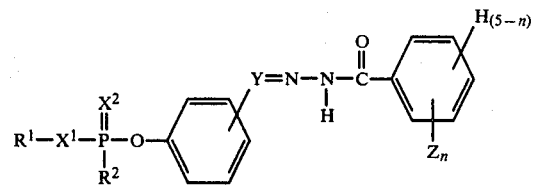

wherein $X^1$ and $X^2$ are each independently selected from the group consisting of oxygen and sulfur; $R^1$ is alkyl; $R^2$ is selected from the group consisting of alkyl, alkoxy and alkylthio; Y is a straight or branched hydrocarbon chain of from 1 to 5 carbon atoms; Z is selected from the group consisting of alkyl, alkenyl, alkoxy, alkylthio, halogen, haloalkyl and nitro; and n is an integer from 0 to 5.

10 Claims, No Drawings

BENZOYLHYDRAZONES OF ARYL PHOSPHATES AND PHOSPHONATES

This invention relates to new compositions of matter and more specifically relates to new chemical compounds of the formula

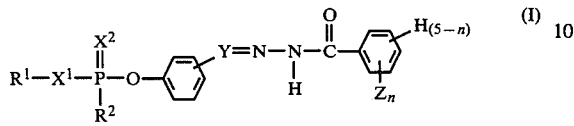

wherein $X^1$ and $X^2$ are each independently selected from the group consisting of oxygen and sulfur; $R^1$ is alkyl; $R^2$ is selected from the group consisting of alkyl, alkoxy and alkylthio; Y is a straight or branched hydrocarbon chain of from 1 to 5 carbon atoms; Z is selected from the group consisting of alkyl, alkenyl, alkoxy, alkylthio, halogen, haloalkyl and nitro; and n is an integer from 0 to 5.

The compounds of the present invention are unexpectedly useful as insecticides.

In a preferred embodiment of the present invention $X^1$ and $X^2$ are each independently selected from the group consisting of oxygen and sulfur; $R^1$ is lower alkyl; $R^2$ is selected from the group consisting of lower alkyl, lower alkoxy and lower alkylthio; Y is a straight or branched hydrocarbon chain of from 1 to 3 carbon atoms; Z is selected from the group consisting of alkyl, alkenyl, alkoxy, alkylthio, halogen, haloalkyl and nitro; and n is an integer from 0 to 3.

The term lower as used herein designates a straight or branched carbon chain of up to six carbon atoms.

The compounds of the present invention can be prepared by reacting an aryl phosphate or phosphonate of the formula

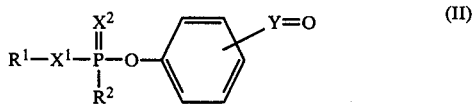

wherein $R^1$, $R^2$, $X^1$, $X^2$ and Y are as heretofore described, with an about equimolar amount of a benzoylhydrazine of the formula

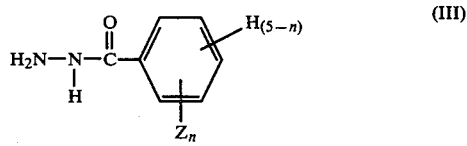

wherein Z and n are as heretofore described. This reaction can be readily effected by combining the compounds of formulae II and III in an inert organic reaction medium such as ethanol and stirring the mixture at room temperature for a period of about 8 to about 24 hours. After this time the desired product can be recovered upon evaporation of the reaction medium or by precipitation upon the addition of water to the reaction product mixture.

The compounds of formula II can be prepared by reacting a chlorophosphate or chlorophosphonate of the formula

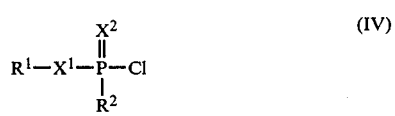

wherein $R^1$, $R^2$, $X^1$ and $X^2$ are as heretofore described, with a hydroxy aldehyde or ketone of the formula

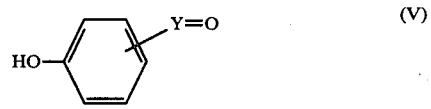

wherein Y is as heretofore described. This reaction can be effected by the slow addition with stirring of a solution of the compound of formula V in an inert organic solvent such as methylene chloride to a solution of an equimolar amount of the compound of formula IV in an inert organic solvent such as methylene chloride, in the presence of an acid acceptor such as a tertiary amine at a temperature of from $-10°$ to $15°$ C. After the addition is completed the reaction mixture can be allowed to warm to room temperature and stirred for an additional period of up to 4 hours to insure completion of the reaction. After this time the reaction product mixture can be washed with dilute aqueous base and with water to remove acid acceptor salt and unrelated starting compounds. The remaining solution can then be stripped of solvent to yield the desired product.

The compounds of formulae III, IV and V are known in the art and are generally available as articles of commerce. The compounds of formula IV when not readily available can be prepared from the corresponding dichlorophosphate or dichlorophosphonate by reaction with the appropriate alkanol.

Exemplary compounds of formula V useful in preparing the compounds of the present invention are 2-hydroxybenzaldehyde, 3-hydroxybenzaldehyde, 4-hydroxybenzaldehyde, 3-hydroxyphenylacetaldehyde, 3-(4-hydroxyphenyl)propionaldehyde, 2-(4-hydroxyphenyl)propionaldehyde, 4(3-hydroxyphenyl)butyaldehyde, 5-(3-hydroxyphenyl)pentanal, 2-hydroxyphenylacetone, 3, hydroxyphenylacetone, 4-hydroxyphenylacetone, 1-(3-hydroxyphenyl)-2-butanone, 4(3-hydroxyphenyl)-2-butanone and the like.

Exemplary compounds of formula IV useful in preparing the compounds of the present invention are dimethyl chlorophosphate, diethyl chlorophosphate, dipropyl chlorophosphate, dibutyl chlorophosphate, dihexyl chlorophosphate, methyl ethyl chlorophosphate, ethyl propyl chlorophosphate, dimethyl chlorothiophosphate, diethyl chlorothiophosphate, dipropyl chlorothiophosphate, ethyl propyl chlorothiophosphate, dihexyl chlorothiophosphate, O-methyl S-ethyl chlorothiophosphate, O-methyl S-propyl chlorothiophosphate, O-ethyl S-propyl chlorothiophosphate, O-ethyl S-butyl thiophosphate, O-ethyl S-propyl chlorodithiophosphate, O-hexyl S-butyl chlorothiophosphate, S,S-dimethyl chlorodithiophosphate, O,S-dimethyl chlorodithiophosphate, O,S-dimethyl chlorodithiophosphate, methyl ethylchlorophosphonate, diethyl chlorophosphonate, S-propyl ethylchlorothiophosphonate, S-butyl ethylchlorothiophosphonate, ethyl butylchlorophosphonate, diethyl chlorothiophosphonate, S-hexyl ethylchlorothiophosphonate, S-ethyl ethylchlorodithiophosphonate and the like.

Exemplary compounds of formula III useful in preparing the compounds of the present invention are benzoylhydrazine, 2-methylbenzoylhydrazine, 3-ethylbenzoylhydrazine, 4-propylbenzoylhydrazine, 4-hexylbenzoylhydrazine, 2-methyl-4-chlorobenzoylhydrazine, 3,4-dichlorobenzoylhydrazine, 4-bromobenzoylhydrazine, 4-fluorobenzoylhydrazine, 3-allylbenzoylhydrazine, 4-pent-3-enylbenzaylhydrazine, 2-methoxybenzoylhydrazine, 3-ethoxybenzoylhydrazine, 3-propoxybenzoylhydrazine, 4-hexyloxybenzoylhydrazine, 3-methylthiobenzoylhydrazine, 2-ethylthiobenzoylhydrazine, 4-butylthiobenzoylhydrazine, 4-hexylthiobenzolylhydrazine, 4-trifluoromethylbenzoylhydrazine, 3-chloromethylbenzoylhydrazine, 3-$\beta$-chloroethylbenzoylhydrazine, $\gamma$-bromopropylbenzoylhydrazine, 3,4-dinitrobenzoylhydrazine, 2,4,6-trichlorobenzoylhydrazine and the like.

The manner in which the compounds of the present invention can be prepared is more specifically illustrated in the following examples.

EXAMPLE 1

Preparation of O-Ethyl S-Propyl Chlorothiophosphate

S-Propyl dichlorothiophosphate (3.1 grams; 0.016 mole) was charged into a 300 ml glass reaction flask equipped with a mechanical stirrer. Methylene chloride (80 ml) was added and the solution was cooled to a temperature of $-10°$ C. A solution of ethanol (0.737 grams; 0.016 mole) and triethylamine (1.62 grams; 0.016 mole) was then added dropwise with stirring while maintaining the temperature of the reaction mixture at about $-5°$ C. After the addition was completed the reaction mixture was allowed to warm to room temperature and stirring was continued for a period of two hours to yield the desired product O-ethyl S-propyl chlorothiophosphate in solution.

EXAMPLE 2

Preparation of O-Ethyl S-Propyl O-(2-Formylphenyl) Thiophosphate

The solution of O-ethyl S-propyl chlorothiophosphate prepared in Example 1 was cooled to 10° C. and triethylamine (1.629 grams; 0.016 mole) was added. A solution of 2-hydroxybenzaldehyde (1.95 grams; 0.016 mole) in methylene chloride (5 ml) was slowly added to the mixture while maintaining the temperature at about 0° C. After this addition was completed the temperature of the reaction mixture was allowed to rise to room temperature and stirring was continued for a period of one hour. After this time the reaction mixture was transferred into a separatory funnel and methylene chloride (100 ml) was added. The resulting solution was washed twice with water (100 ml), twice with aqueous sodium hydroxide (0.1 N; 50 ml) and again twice with water (100 ml). The washed solution was then dried over anhydrous magnesium sulfate, filtered and stripped of solvent under vacuum in a rotary evaporator leaving a light orange oil as the residue. This oil was placed under high vacuum for a period of one hour to yield the desired product as a yellow oil.

EXAMPLE 3

Preparation of O-Ethyl S-Propyl O-[2-(Benzoylhydrazonomethyl)phenyl] Thiophosphate A solution of O-ethyl S-propyl O-(2-formylphenyl) thiophosphate (4.1 grams; 0.0142 mole) in methanol (50 ml) was charged into a glass reaction vessel equipped with a mechanical stirrer. Benzoylhydrazine (1.939 grams; 0.0142 mole) was added and the reaction mixture was stirred at room temperature overnight. After this time water was added to the reaction mixture until it became cloudy. The mixture was then heated on a steam bath until it became clear again. The reaction mixture was then cooled in an ice bath resulting in the formation of a solid precipitate. The precipitate was recovered by filtration and washed with isopropyl ether. The washed product was then air dried for 15 minutes and thereafter dried overnight in a vacuum oven to yield the desired product O-ethyl S-propyl O-[2-benzoylhydrazonomethyl)phenyl] thiophosphate as a white powder.

EXAMPLE 4

Preparation of O-Ethyl S-Propyl O-(4-Formylphenyl) Thiophosphate

The potassium salt of 4-hydroxybenzaldehyde (2.88 grams; 0.018 mole) and a solution of O-ethyl S-propyl thiophosphoryl chloride (0.018 mole) in acetonitrile (75 ml) were charged into a glass reaction vessel equipped with a mechanical stirrer. The mixture was stirred overnight. After this time the reaction mixture was filtered and stripped of solvent under reduced pressure having a viscous oil. This oil was dissolved in diethyl ether. The ether solution was filtered to remove insolubles and the filtrate was stripped of solvents under vacuum to yield the desired product O-ethyl S-propyl O-(4-formylphenyl) thiophosphate as a dark red oil.

EXAMPLE 5

Preparation of O-Ethyl S-Propyl O-[4-(Benzoylhydrazonomethyl)phenyl]Thiophosphate O-Ethyl S-propyl O-(4-formylphenyl) thiophosphate (5.44 grams; 0.019 mole), ethanol (150 ml) and benzoylhydrazine (2.57 grams; 0.019 mole) were charged into a glass reaction vessel equipped with a mechanical stirrer. The reaction mixture was stirred at room temperature overnight. The reaction mixture was then stripped of ethanol under reduced pressure having a viscous oil as the residue. The residue was then dissolved in diethyl ether resulting in the formation of a precipitate. The ether solution was decanted from the precipitate and was stripped of solvent under vacuum leaving an orange-brown oil. This oil was chromatographed on a silica gel column using methylene chloride and methylene chloride-acetone mixtures as the eluant. Fourteen fractions were recovered and fractions 3 plus 4, 7, 8 and 9 were analyzed by infra red spectroscopy revealing that fraction 8 was the desired product. This fraction was stripped of solvent to yield the desired product O-ethyl S-propyl O-[4-(benzoylhydrazonomethyl)phenyl] thiophosphate as a yellow oil.

EXAMPLE 6

Preparation of O-Ethyl S-Propyl O-(3-Formuylphenyl) Thiophosphate

A solution of O-ethyl S-propyl chlorothiophosphate prepared by the method detailed in Example 1 was charged into a glass reaction vessel equipped with a stirrer and thermometer. The solution was cooled to a temperature of about $-10°$ C. and triethylamine (2.23 ml) was added followed by the dropwise addition with stirring of 3-hydroxybenzaldehyde (1.95 grams; 0.016 mole) dissolved in methylene chloride (10 ml). Stirring was continued for a period of about 2 hours while maintaining the temperature of the reaction mixture at about 0° C. After this time the reaction mixture was transferred into a separatory funnel and was washed twice with water (100 ml), twice with dilute aqueous sodium hydroxide (50 ml; 0.1 N) and again twice with water (100 ml). The washed solution was then dried over anhydrous magnesium sulfate, filtered and stripped of solvent leaving an orange oil. This oil was subjected to high vacuum for a period of one hour to yield the desired product O-ethyl S-propyl O-(3-formylphenyl) thiophosphate.

EXAMPLE 7

Preparation of O-Ethyl S-Propyl O-[3-(Benzoylhydrazonomethyl)phenyl] Thiophosphate O-Ethyl S-propyl O-(3-formylphenyl) thiophosphate (6.0 grams; 0.016 mole), ethanol (100 ml) and benzoylhydrazine (2.18 grams; 0.016 mole) were charged into a glass reaction vessel equipped with a mechanical stirrer. The reaction mixture was stirred at room temperature overnight. After this time the reaction mixture was stripped of methanol leaving an orange oil. This oil was dissolved in methylene chloride and the resulting solution was washed twice with water (100 ml), twice with aqueous sodium hydroxide (50 ml; 0.1 N) and again twice with water (100 ml). The washed solution was then dried over anhydrous magnesium sulfate and was stripped of solvent under vacuum to yield the desired product O-ethyl S-propyl O-[3-(benzoylhydrazonomethyl)phenyl]thiophosphate as a viscous orange oil.

EXAMPLE 8

Preparation of O-Methyl S-Ethyl O-(4-Formylphenyl) Thiophosphate

A solution of O-methyl S-ethyl chlorothiophosphate (0.03 mole) in methylene chloride (50 ml) is charged into a glass reaction vessel equipped with a mechanical stirrer. Triethylamine (0.03 mole) is added and the mixture is cooled to a temperature of about 0° C. A solution of 4-hydroxybenzaldehyde (0.03 mole) in methylene chloride (15 ml) is slowly added with stirring while maintaining the temperature of the reaction mixture at about 0° C. After the addition is completed the reaction mixture is allowed to warm to room temperature and stirring is continued for a period of about 1 hour. After this time the reaction mixture is transferred to a separatory funnel and methylene chloride (100 ml) is added. The resulting solution is then washed with water, dilute aqueous sodium hydroxide and again with water. The washed solution is dried over anhydrous magnesium sulfate, is filtered and stripped of solvent under vacuum to yield the desired product O-methyl S-ethyl O-(4-formylphenyl) thiophosphate.

EXAMPLE 9

Preparation of O-Methyl S-Ethyl O-[4-(3-Chlorobenzoylhydrazonomethyl)phenyl] Thiophosphate A solution of O-methyl S-ethyl O-(4-formylphenyl) thiophosphate (0.02 mole) in methanol (50 ml) and 3-chlorobenzoylhydrazine (0.02 mole) are charged into a glass reaction vessel and the mixture is stirred at room temperature for a period of about 12 hours. After this time the reaction mixture is stripped of methanol under vacuum and the residue is dissolved in methylene chloride (100 ml) and the resulting solution is washed with water (75 ml), with aqueous sodium hydroxide (75 ml; 0.1 N) and again with water (75 ml). The washed solution is then dried over anhydrous magnesium sulfate, filtered and stripped of solvent to yield the desired product O-methyl S-ethyl O-[4-(3-chlorobenzoylhydrazonomethyl)phenyl] thiophosphate.

EXAMPLE 10

Preparation of O,O-Dibutyl O-(3-Formylphenyl) Thiophosphate

A solution of O,O-dibutyl chlorothiophosphate (0.03 mole) in methylene chloride (50 ml) is charged into a glass reaction vessel equipped with a mechanical stirrer. Triethylamine (0.03 mole) is added and the mixture is cooled to a temperature of about 0° C. A solution of 3-hydroxybenzaldehyde (0.03 mole) in methylene chloride (15 ml) is slowly added with stirring while maintaining the temperature of the reaction mixture at about 0° C. After the addition is completed the reaction mixture is allowed to warm to room temperature and stirring is continued for a period of about 1 hour. After this time the reaction mixture is transferred to a separatory funnel and methylene chloride (100 ml) is added. The resulting solution is then washed with water, dilute aqueous sodium hydroxide and again with water. The washed solution is dried over anhydrous magnesium sulfate, is filtered and stripped of solvent under vacuum to yield the desired product O,O-dibutyl O-(3-formylphenyl) thiophosphate.

EXAMPLE 11

Preparation of O,O-Dibutyl O-[3-(4-Methylbenzoylhydrazonomethyl)phenyl] Thiophosphate A solution of O,O-dibutyl O-(3-formylphenyl) thiophosphate (0.02 mole) in methanol (50 ml) and 4-methylbenzoylhydrazine (0.02 mole) are charged into a glass reaction vessel and the mixture is stirred at room temperature for a period of about 12 hours. After this time the reaction mixture is stripped of methanol under vacuum and the residue is dissolved in methylene chloride (100 ml) and the resulting solution is washed with water (75 ml), with aqueous sodium hydroxide (75 ml; 0.1 N) and again with water (75 ml). The washed solution is then dried over anhydrous magnesium sulfate, filtered and stripped of solvent to yield the desired product O,O-dibutyl O-[3-(4-methylbenzoylhydrazonomethyl)phenyl] thiophosphate.

EXAMPLE 12

Preparation of S-Propyl O-(2-Formylphenyl) Ethylthiophosphonate

A solution of S-propyl ethylthiophosphonate (0.03 mole) in methylene chloride (50 ml) is charged into a glass reaction vessel equipped with a mechanical stirrer. Triethylamine (0.03 mole) is added and the mixture is cooled to a temperature of about 0° C. A solution of 2-hydroxybenzaldehyde (0.03 mole) in methylene chloride (15 ml) is slowly added with stirring while maintaining the temperature of the reaction mixture at about 0° C. After the addition is completed the reaction mixture is allowed to warm to room temperature and stirring is continued for a period of about 1 hour. After this time the reaction mixture is transferred to a separatory funnel and methylene chloride (100 ml) is added. The resulting solution is then washed with water, dilute aqueous sodium hydroxide and again with water. The washed solution is dried over anhydrous magnesium sulfate, is filtered and stripped of solvent under vacuum to yield the desired product S-propyl O-(2-formylphenyl) ethylthiophosphate.

EXAMPLE 13

Preparation of S-Propyl O-[2-(4-Trifluoromethylbenzolylhydrazonomethyl)-phenyl] Ethylthiophosphonate A solution of S-propyl O-(2-formylphenyl) ethylthiophosphonate (0.02 mole) in methanol (50 ml) and 4-trifluoromethylbenzoylhydrazine (0.02 mole) are charged into a glass reaction vessel and the mixture is stirred at room temperature for a period of about 12 hours. After this time the reaction mixture is stripped of methanol under vacuum and the residue is dissolved in methylene chloride (100 ml) and the resulting solution is washed with water (75 ml) with aqueous sodium hydroxide (75 ml; 0.1 N) and again with water (75 ml). The washed solution is then dried over anhydrous magnesium sulfate, filtered and stripped of solvent to yield the desired product S-propyl O-[2-(4-trifluoromethylbenzoylhydrazonomethyl)phenyl] ethylthiophosphonate.

EXAMPLE 14

Preparation of S-Ethyl S-Hexyl O-(3-Formylmethylphenyl) Dithiophosphate

A solution of S-ethyl S-hexyl chlorodithiophosphate (0.03 mole) in methylene chloride (50 ml) is charged into a glass reaction vessel equipped with a mechanical stirrer. Triethylamine (0.03 mole) is added and the mixture is cooled to a temperature of about 0° C. A solution of 3-hydroxylphenylacetaldehyde (0.03 mole) in methylene chloride (15 ml) is slowly added with stirring while maintaining the temperature of the reaction mixture at about 0° C. After the addition is completed, the reaction mixture is allowed to warm to room temperature and stirring is continued for a period of about 1 hour. After this time the reaction mixture is transferred to a separatory funnel and methylene chloride (100 ml) is added. The resulting solution is then washed with water, dilute aqueous sodium hydroxide and again with water. The washed solution is dried over anhydrous magnesium sulfate, is filtered and stripped of solvent under vacuum to yield the desired product S-ethyl S-hexyl O-(3-formylmethylphenyl) dithiophosphate.

EXAMPLE 15

Preparation of S-Ethyl S-Hexyl O-{3-[2-(3-Allylbenzoylhydrazono)ethyl]phenyl} Dithiophosphate A solution of S-ethyl S-hexyl O-(3-Formylmethylphenyl) dithiophosphate (0.02 mole) in methanol (50 ml) and 3-allylbenzoylhydrazine (0.02 mole) are charged into a glass reaction vessel and the mixture is stirred at room temperature for a period of about 12 hours. After this time the reaction mixture is stripped of methanol under vacuum and the residue is dissolved in methylene chloride (100 ml) and the resulting solution is washed with water (75 ml), with aqueous sodium hydroxide (75 ml; 0.1 N) and again with water (75 ml). The washed solution is then dried over anhydrous magnesium sulfate, filtered and stripped of solvent to yield the desired product S-ethyl S-hexyl O-{3-[2-(3-allylbenzoylhydrazono)ethyl]phenyl} dithiophosphate.

EXAMPLE 16

Preparation of O-Propyl S-Ethyl O-(4-Acetylphenyl) Dithiophosphate

A solution of O-propyl S-ethyl chlorodithiophosphate (0.03 mole) in methylene chloride (50 ml) is charged into a glass reaction vessel equipped with a mechanical stirrer. Triethylamine (0.03 mole) is added and the mixture is cooled to a temperature of about 0° C. A solution of p-hydroxyacetophenane (0.03 mole) in methylene chloride (15 ml) is slowly added with stirring while maintaining the temperature of the reaction mixture at about 0° C. After the addition is completed, the reaction mixture is allowed to warm to room temperature and stirring is continued for a period of about 1 hour. After this time the reaction mixture is transferred to a separatory funnel and methylene chloride (100 ml) is added. The resulting solution is then washed with water, dilute aqueous sodium hydroxide and again with water. The washed solution is dried over anhydrous magnesium sulfate, is filtered and stripped of solvent under vacuum to yield the desired product O-propyl S-ethyl O-(4-acetylphenyl) dithiophosphate.

EXAMPLE 17

Preparation of O-Propyl S-Ethyl O-{4-[1-(2-Methoxybenzoylhydrazono)ethyl]-phenyl} Dithiophosphate A solution of O-propyl S-ethyl O-(4-autylphenyl) dithiophosphate (0.02 mole) in methanol (50 ml) and 2-methoxybenzoylhydrazine (0.02 mole) are charged into a glass reaction vessel and the mixture is stirred at room temperature for a period of about 12 hours. After this time the reaction mixture is stripped of methanol under vacuum and the residue is dissolved in methylene chloride (100 ml) and the resulting solution is washed with water (75 ml), with aqueous sodium hydroxide (75 ml; 0.1 N) and again with water (75 ml). The washed solution is then dried over anhydrous magnesium sulfate, filtered and stripped of solvent to yield the desired product O-propyl S-ethyl O-{4-[1-(2-methoxybenzolylhydrazono)ethyl]phenyl} diothiophosphate.

EXAMPLE 18

Preparation of O-Propyl O-[3-(Formylpropyl)phenyl] Hexylphosphonate

A solution of O-propyl hexylchlorophosphonate (0.03 mole) in methylene chloride (50 ml) is charged into a glass reaction vessel equipped with a mechanical stirrer. Triethylamine (0.03 mole) is added and the mixture is cooled to a temperature of about 0° C. A solution of 4-(3-hydroxyphenyl)butyraldehyde (0.03 mole) in methylene chloride (15 ml) is slowly added with stirring while maintaining the temperature of the reaction mixture at about 0° C. After the addition is completed the reaction mixture is allowed to warm to room temperature and stirring is continued for a period of about 1 hour. After this time the reaction mixture is transferred to a separatory funnel and methylene chloride (100 ml) is added. The resulting solution is then washed with water, dilute aqueous sodium hydroxide and again with water. The washed solution is dried over anhydrous magnesium sulfate, is filtered and stripped of solvent under vacuum to yield the desired product O-propyl O-[3-(3-formylpropyl)phenyl]hexylphosphonate.

EXAMPLE 19

Preparation of O-Propyl O-{3-[4-(4-Methylthiobenzoylhydrazono)butyl]phenyl} Hexylphosphonate A solution of O-propyl O-[3-(3-formylpropyl)phenyl] hexylphosphonate (0.02 mole) in methanol (50 ml) and 4-methylthiobenzoylhydrazine (0.02 mole) are charged into a glass reaction vessel and the mixture is stirred at room temperature for a period of about 12 hours. After this time the reaction mixture is stripped of methanol under vacuum and the residue is dissolved in methylene chloride (100 ml) and the resulting solution is washed with water (75 ml), with aqueous sodium hydroxide (75 ml; 0.1 N) and again with water (75 ml). The washed solution is then dried over anhydrous magnesium sulfate, filtered and stripped of solvent to yield the desired product O-propyl O-{3-[4(4-methylthiobenzoylhydrazono)butyl]phenyl} hexylphosphonate.

EXAMPLE 20

Preparation of S-Ethyl S-Propyl O-(2-Formylphenyl) Trithiophosphate

A solution of S-ethyl S-propyl chlorotrithiophosphate (0.03 mole) in methylene chloride (50 ml) is charged into a glass reaction vessel equipped with a mechanical stirrer. Triethylamine (0.03 mole) is added and the mixture is cooled to a temperature of about 0° C. A solution of 2-hydroxybenzaldehyde (0.03 mole) in methylene chloride (15 ml) is slowly added with stirring while maintaining the temperature of the reaction mixture at about 0° C. After the addition is completed the reaction mixture is allowed to warm to room temperature and stirring is continued for a period of about 1 hour. After this time the reaction mixture is transferred to a separatory funnel and methylene chloride (100 ml) is added. The resulting solution is then washed with water, dilute aqueous sodium hydroxide and again with water. The washed solution is dried over anhydrous magnesium sulfate, is filtered and stripped of solvent under vacuum to yield the desired product S-ethyl S-propyl O-(2-formylphenyl)trithiophosphate.

EXAMPLE 21

Preparation of S-Ethyl S-Propyl O-[2-(4-Nitrobenzoylhydrazonomethyl)phenyl] Trithiophosphate A solution of S-ethyl S-propyl O-(2-formylphenyl) trithiophosphate (0.02 mole) in methanol (50 ml) and 4-nitrobenzoylhydrazine (0.02 mole) are charged into a glass reaction vessel and the mixture is stirred at room temperature for a period of about 12 hours. After this time the reaction mixture is stripped of methanol under vacuum and the residue is dissolved in methylene chloride (100 ml) and the resulting solution is washed with water (75 ml), with aqueous sodium hydroxide (75 ml; 0.1 N) and again with water (75 ml). The washed solution is then dried over anhydrous magnesium sulfate, filtered and stripped of solvent to yield the desired product S-ethyl S-propyl O-[2-(4-nitrobenzoylhydrazonomethyl)phenyl] trithiophosphate.

Additional exemplary compounds within the scope of the present invention which can be prepared by the procedures detailed in the foregoing examples are the following.

O-methyl O-[2-(2-ethylbenzoylhydrazonomethyl)phenyl] methylphosphonate

O-propyl O-[2-(4-t-butylbenzoylhydrazonomethyl)phenyl] propylphosphonate

O-hexyl S-methyl O-[3-(3-hexylbenzoylhydrazonomethyl)phenyl] thiophosphate

O-ethyl S-butyl O-{4-[3-(but-3-enylbenzoylhydrazono)propyl]phenyl} thiophosphate O-ethyl S-propyl O-{4-[5-(hex-4-enylbenzoylhydrazono)pentyl]phenyl} thiophosphate O-ethyl S-propyl O-[3-(4-hexylbenzoylhydrazonomethyl)phenyl] thiophosphate O-ethyl S-propyl O-[3-(3-ethylthiobenzoylhydrazonomethyl)phenyl] thiophosphate O-ethyl S-propyl O-[4-(3-propylthiobenzoylhydrazonomethyl)phenyl] thiophosphate O-ethyl S-propyl O-[3-(4-ethoxybenzoylhydrazonomethyl)phenyl] thiophosphate O-ethyl S-propyl O-[2-(4-propoxybenzoylhydrazonomethyl)phenyl] thiophosphate O-ethyl S-propyl O-[3-(4-hexyloxybenzoylhydrazonomethyl)phenyl] thiophosphate O-ethyl S-propyl O-[4-(3-hexylthiobenzoylhydrazonomethyl)phenyl] thiophosphate O-ethyl S-propyl O-[4-(3,4-dibromobenzoylhydrazonomethyl)phenyl] thiophosphate O-ethyl S-propyl O-[4-(4-fluorobenzoylhydrazonomethyl)phenyl] thiophosphate O-ethyl S-propyl O-[4-(3-β-chloroethylbenzoylhydrazonomethyl)phenyl] thiophosphate O-ethyl S-propyl O-[4-(2,4,6-trichlorobenzoylhydrazonomethyl)phenyl] thiophosphate.

For practical use as insecticides, the compounds of this invention are generally incorporated into insecticidal compositions which comprise an inert carrier and an insecticidally toxic amount of such a compound. Such insecticidal compositions, which can also be called formulations, enable the active compound to be applied conveniently to the site of the insect infestation in any desired quantity. These compositions can be solids, such as dusts, granules or wettable powders; or they can be liquids such as solutions, aerosols or emulsifiable concentrates.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the active compounds are sufficiently soluble in common organic solvent such as kerosene or xylene so that they can be used directly as solutions in these solvents. Frequently, solutions of insecticides can be dispersed under superatmospheric pressure as aerosols. However, preferred liquid insecticidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the insect infestation. The emulsifiers most commonly used in these concentrates are nonionic or mixture of nonionic with anionic surface-active agents.

A typical insecticidal composition according to this invention is illustrated by the following example, in which the quantities are in parts by weight.

EXAMPLE 22

Preparation of a Dust

Product of Example 1: 10
Powdered talc: 90

The above ingredients are mixed in a mechanical grinder-blender and are ground until a homogeneous, freeflowing dust of the desired particle size is obtained. This dust is suitable for direct application to the site of the insect infestation.

The compounds of this invention can be applied as insecticides in any manner recognized by the art. One method for destroying insects comprises applying to the locus of the insect infestation, an insecticidal composition comprising an inert carrier and, as the essential active ingredient, in a quantity which is toxic to said insects, a compound of the present invention. The concentration of the new compounds of this invention in the insecticidal compositions will vary greatly with the type of formulation and the purpose for which it is designed, but generally the insecticidal compositions will comprise from about 0.05 to about 95 percent by weight of the active compounds of this invention. In a preferred embodiment of this invention, the insecticidal compositions will comprise from about 5 to 75 percent by weight of the active compound. The compositions can also comprise such additional substances as other pesticides, stabilizers, spreaders, deactivators, adhesives, stickers, fertilizers, activators, synergists and the like.

The compounds of the present invention are also useful when combined with other insecticides in the insecticidal compositions heretofore described. These other insecticides can comprise from about 5 to 95 percent of the active ingredients in the insecticidal compositions. Use of the combinations of these other insecticides with the compounds of the present invention provide insecticidal compositions which are more effective in controlling insects and often provide results unattainable with separate compositions of the individual insecticides. The other insecticides with which the compounds of this invention can be used in the insecticidal compositions to control insects, can include halogenated compounds such as DDT, methoxychlor, TDE, lindane, chlordane, isobenzan, aldrin, dieldrin, heptachlor, endrin, mirex, endosulfon, dicofol and the like; organic phosphorus compounds such as TEPP, schradan, ethion, parathion, methyl parathion, PEN, demeton, carbophenothion phorate, zinophos, diazinon, malathion, mevinphos, dimethoate, DBD, ronnel, oxydemeton-methyl, dicapthon, chlorothion, phosphamidon, naled, fenthion, trichlorofon, DDVP and the like; organic nitrogen compounds such as dinitro-O-cresol, dinitrocyclohexylphenol, DNB, DNP, binapacril, azobenzene and the like; organic carbamate compounds such as carbaryl, ortho 5353 and the like, organic sulfur compounds such as phenothiazine, phenoxathin, lauryl thiocyanate, bis(2-thiocyanoethyl)ether, isobornyl thiocyanoacetate and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide paradichlorobenzene and the like.

The compounds of the present invention can also be combined with fungicidal and nematocidal chemical compounds to form pesticidal compositions useful for the control of fungi and in some cases soil nematodes as well as insects. Typical examples of such fungicidal chemical compounds are ferbam, nabam, zineb, ziram, thiram, chloranil, dichlone, glyodin, cycloheximide, dinocap, maneb, captan, dodine, PCNB, p-dimethylaminobezenediazo sodium sulfonate and the like; while examples of nematocidal compounds are chloropicrin O,O-diethyl O-(2,4-dichlorophenyl) phosphorothioate, tetrachlorothiophene, dazomet, dibromochloropropane and the like.

The new compounds of this invention can be used in many ways for the control of insects. Insecticides which are to be used as stomach poisons or protective materials can be applied to the surface on which the insects feed or travel. Insecticides which are to be used as contact poisons or eradicants can be applied directly to the body of the insect, as a residual treatment to the surface on which the insect may walk or crawl, or as a fumigant treatment of the air which the insect breathes. In some cases, the compounds applied to the soil or plants surfaces are taken up by the plant, and the insects are poisoned systematically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects, such as the Mexican bean beetle and the southern armyworm; the piercing-sucking insects, such as the pea aphid, the cereal leaf beetle, the housefly, the grape leafhopper, the chinch bug, the lygus bug, the oyster shell scale, the California red scale, the Florida red scale, the soft scale and mosquitoes; the internal feeders, including borers, such as the European corn borer, the peach twig borer and the corn earworm, worms of weevils such as the codling moth, the alfalfa weevil, the cotton boll weevil, the pink boll worm, the plum curculio, the red banded leaf roller, the melonworm, the cabbage looper and the apple maggot, leaf miners such as the apple leaf miner, the birch leaf miner and the beet leaf miner, and gall insects such as the wheat joint worm and the grape phylloxera. Insects which attack below the surface of the ground are classified as subterranean insects and include such destructive pests as the woolly apple aphid, the Japanese beetle, the onion maggot and the corn rootworm.

The quantity of active compound of this invention to be used for insect control will depend on a variety of factors, such as the specific insect involved, intensity of the infestation, weather, type of environment, type of formulation and the like. For example, the application of only one or two ounces of active chemical per acre may be adequate for control of a light infestation of an insect under conditions unfavorable for its feeding, while a pound or more of active compound per acre may be required for the control of a heavy infestation of insects under conditions favorable to their development.

The insecticidal activity of the compounds of the present invention was demonstrated by experiments carried out for the control of a variety of insects. In these experiments, the compounds to be tested are first put into a formulation suitable for application at various concentrations and application rates to plants and insects. The desired quantity of the test compound (the quantity being determined by the application concentration or application rate to be used in later testing) is dissolved or dispersed in a solvent consisting of acetone containing 3.19 grams/liter of Triton ®X-155 (alkylaryl polyether alcohol). When it has dissolved or dispersed in the acetone, 4 volumes of the acetone solution or dispersion are diluted with 96 volumes of distilled water. (If the test compound is insoluble in the acetone or distilled water it can be dispersed using a tissue grinder.) Lower concentration test solutions may be made by dilution of higher concentration solutions with a diluent consisting of 96 volumes distilled water and 4 volumes of acetone containing 3.19 grams of Triton ®X-155 per liter.

Test plants used in these experiments are prepared by planting the appropriate seeds in sterilized soil contained in plastic pots having an upper soil surface area of approximately 12.25 square inches (a square pot having a 3.5 inch side). After the seed has been planted, a layer of approximately 0.25 inches of sand is spread on the top surface of the soil. The test compound is applied after the plant has reached a specified size.

For foliar applications, the test compound, dissolved or dispersed in the water/acetone solvent described above, is sprayed as a mist onto the foliage of the test plants. The concentration of the test compound and the total quantity of solution applied is adjusted to give the application concentrations or rates desired. The plants are then allowed to air dry. Mites and aphids are exposed to treated leaves which have been left on the plant. Other insect species are exposed to treated leaves which have been removed from the plant and placed in petri dishes containing a piece of moist filter paper.

For soil drench applications, the test compound is first dissolved or dispersed in water/acetone as described above, then the amount of solution required to give a desired application rate is applied, using a pipette, evenly over the top of the soil in the pot. Twenty-four hours after the treatment, mites and aphids are exposed to leaves which have been left on the treated plants. Other insects species are exposed to leaves which have been removed from the plant and placed in petri dishes containing a piece of moist filter paper.

In direct contact applications, the test compound is, again, first formulated into a water/acetone solution, as described above, in the concentrations to be tested. Then the insect to be tested is dipped into, sprayed with or immersed in the liquid, dried and observed for effect.

In the tables below setting forth the experimental data, PPM represents foliar application rates expressed as parts-per-million.

CABBAGE LOOPER

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten cabbage loopers, second instar larval stage, are placed in each petri dish and the dish covered. Observations of insect mortality are made after 48 hours of exposure.

SOUTHERN ARMYWORM

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten southern armyworms, second instar larval stage, are placed in each petri dish and the dish covered. Observations of insect mortality are made after 48 hours of exposure.

SOYBEAN LOOPER

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten second instar larval soybean loopers are placed in each petri dish and the dish covered. Observations of insect mortality are made after 48 hours of exposure.

TOBACCO BUDWORM

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten tobacco budworms, second instar larval stage, are placed in each petri dish and the dish covered. Observations of insect mortality are made after 48 hours of exposure.

MEXICAN BEAN BEETLE

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten Mexican bean beetles, second instar larval stage, are placed in each petri dish and the dish covered. Observations of insect mortality are made after 48 hours of exposure.

PEA APHID

Pea plants (Burpee Wando) in the 10–14 day stage are treated with the test compound, at various application rates, both by foliar spray and soil drench methods. The plants are air-dried for about 30 minutes after the foliar spray is applied, then 25–50 pea aphids, adults and nymphs, are put on each treated plant and on an untreated control plant with a small paint brush. Twenty-four hours after a plant has been treated by the soil drench method, it is infested by 25–50 aphids using the technique described above. An untreated control plant is similarly infested. After 48 hours of exposure of the insects to the treated plants, insect mortality is determined by comparison of the number of insects on the treated plants to the number of the untreated control plant.

HOUSEFLY

Ten adult Houseflies are placed in a small (2"-3") wire screen cage fitted with a plastic cap. The cage is sprayed with the test compound at the desired concentration in the form of a solution prepared as described hereinabove. After spraying, the treated cages are stored until dry. Sixty minutes after spraying, readings are made of knock down. The cages are then placed on paper toweling moistened with 5-10% sucrose solution and stored on this toweling for 23 hours at which time the 24 hours-after-treatment mortality reading is taken.

GERMAN COCKROACH

Solutions of test compounds are formulated as described hereinbefore and the solution which gives a desired application concentration is placed in a flask. Ten German cockroach adults are placed in a teaspoon tea strainer and are dipped into the test solution. The excess solution is shaken off, the tea strainer opened and the insects placed in a clear plastic container containing a small moist piece of dental wick. The container then is capped with a cover pierced with air holes. Insect mortality is observed 60 minutes an 24 and 48 hours after the exposure.

We claim:

1. A compound of the formula

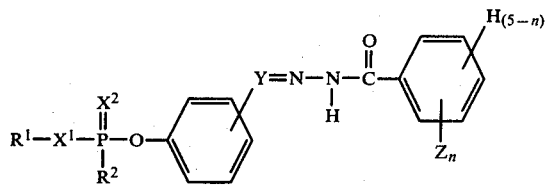

wherein $X^1$ and $X^2$ are each independently selected from the group consisting of oxygen and sulfur; $R^1$ is alkyl; $R^2$ is selected from the group consisting of alkyl, alkoxy and alkylthio; Y is a straight or branched hydrocarbon chain of from 1 to 5 carbon atoms; Z is selected from the group consisting of lower alkyl, lower alkenyl, lower alkoxy, lower alkylthio, halogen, haloloweralkyl and nitro; and n is an integer from 0 to 5.

2. The compound of claim 1, O-ethyl S-propyl O-[2-(benzoylhydrazonomethyl)phenyl] thiophosphate.

3. The compound of claim 1, O-ethyl S-propyl O-[4-benzoylhydrazonomethyl)phenyl] thiophosphate.

4. The compound of claim 1, O-ethyl S-propyl O-[3-benxoylhydrazonomethyl)phenyl] thiophosphate.

5. The compound of claim 1, O-methyl S-ethyl O-[4-(3-chlorobenzoylhydrazonomethyl)phenyl] thiophosphate.

6. The compound of claim 1, O-O-dibutyl O-[3-(4-methylbenzoylhydrazonomethyl)phenyl] thiophosphate.

7. The compound of claim 1, S-propyl O-[2-(4-trifluoromethylbenzoylhydrazonomethyl)phenyl] ethyl-

TABLE I

| Test Compound | Concentration PPM | CAL | SAW | SBL | TBW | % Mortality MBB | PA | HF 60 min | 24 hrs | GCR 60 min | 24 hrs | 48 hrs |
|---|---|---|---|---|---|---|---|---|---|---|---|---|
| Prod. of Ex. 3 | 256 | 80 | 100 | 100 | 100 | — | — | — | — | — | — | — |
|  | 128 | 92.5(4) | 100(3) | 100 | 92.5(4) | 100 | 80 | 100 | 50 | 0 | 0 | 0 |
|  | 64 | 68.5(4) | 100(3) | 80 | 80(4) | 100 | 50 | 100 | 40 | 0 | 0 | 0 |
|  | 32 | 56.6(3) | 60(2) | — | 76.6(3) | 70 | 50 | 100 | 100 | 0 | 0 | 0 |
|  | 16 | 25(2) | 0 | — | 30(2) | — | — | — | — | — | — | — |
| Prod. of Ex. 5 | 256 | 100 | 100 | 100 | 90 | — | — | — | — | — | — | — |
|  | 128 | 90(2) | 95(2) | 100 | 100(2) | — | — | — | — | — | — | — |
|  | 64 | 45(2) | 75(2) | 30 | 75(2) | — | — | — | — | — | — | — |
|  | 32 | 20 | 0 | — | 90 | — | — | — | — | — | — | — |
|  | 16 | 20 | 0 | — | 20 | — | — | — | — | — | — | — |
| Control | 0 | 7.6(4) | 0 | 0 | 2.5(4) | 0 | 0 | 30 | 50 | 0 | 0 | 0 |

(2)average of two separate experiments
(3)average of three separate experiments
(4)average of four separate experiments
CAL = Cabbage looper
SAW = Southern armyworm
SBL = Soybean looper
TBW = Tobacco budworm
MBB = Mexican bean beetle
PA = Pea aphid
HF = House fly
GCR = German cockroach thiophosphate.

8. The compound of claim 1, S-ethyl S-hexyl O-{3-[2-(3-allylbenzoylhydrazono)ethyl]phenyl} dithiophosphate.

9. An insecticidal composition comprising an inert carrier and as an essential active ingredient, in a quantity toxic to insects, a compound of claim 1.

10. A method of controlling insects comprising contacting said insects or the locus of said insects with an insecticidal composition of claim 9.

* * * * *